United States Patent [19]
Goodfellow et al.

[11] Patent Number: 5,356,434
[45] Date of Patent: Oct. 18, 1994

[54] ARTIFICIAL LIGAMENTS

[75] Inventors: John W. Goodfellow, Woodeaton; John J. O'Connor, Headington, both of England

[73] Assignee: British Technology Group Limited, London, England

[21] Appl. No.: 949,504

[22] PCT Filed: May 22, 1991

[86] PCT No.: PCT/GB91/00804
§ 371 Date: Nov. 17, 1992
§ 102(e) Date: Nov. 17, 1992

[87] PCT Pub. No.: WO91/17719
PCT Pub. Date: Nov. 28, 1991

[30] Foreign Application Priority Data
May 22, 1990 [GB] United Kingdom ............... 9011435

[51] Int. Cl.5 ............................................. A61F 2/08
[52] U.S. Cl. ................................. 623/13; 623/18
[58] Field of Search ............... 623/11, 12, 13, 14, 623/15, 16, 18

[56] References Cited

U.S. PATENT DOCUMENTS

| | | | |
|---|---|---|---|
| 3,613,120 | 10/1971 | McFarland . | |
| 3,699,969 | 10/1972 | Mlen .................. | 623/15 |
| 3,831,202 | 8/1974 | Hulsen ................ | 623/15 |
| 3,973,277 | 8/1976 | Semple et al. ...... | 623/13 |
| 4,149,277 | 4/1979 | Bokros ............... | 623/15 |
| 4,345,339 | 8/1982 | Muller . | |
| 4,401,107 | 8/1983 | Haber et al. ........ | 623/14 |
| 4,530,113 | 7/1985 | Matterson . | |
| 4,553,271 | 11/1985 | Baker ................. | 623/14 |
| 4,584,722 | 4/1986 | Levy et al. .......... | 623/13 |
| 4,775,380 | 10/1988 | Seedhom et al. . | |
| 5,176,708 | 1/1993 | Frey et al. .......... | 623/13 |
| 5,192,322 | 3/1993 | Koch et al. ......... | 623/13 |

FOREIGN PATENT DOCUMENTS

| | | |
|---|---|---|
| 0041111 | 12/1981 | European Pat. Off. . |
| 126448 | 11/1984 | European Pat. Off. . |
| 223370 | 5/1987 | European Pat. Off. . |
| 0278713 | 8/1988 | European Pat. Off. . |
| 437174 | 7/1991 | European Pat. Off. . |
| 0255408 | 4/1987 | France . |
| 1465744 | 3/1977 | United Kingdom . |
| 2151487 | 7/1985 | United Kingdom . |
| 2244217 | 11/1991 | United Kingdom . |
| 89/01320 | 2/1989 | World Int. Prop. O. . |

Primary Examiner—David Isabella
Attorney, Agent, or Firm—Cushman, Darby & Cushman

[57] ABSTRACT

An artificial ligament (10) has a bundle of coextensive elongate elements (11) held at their opposite ends in a mutual one-to-one relationship with the relative disposition of the individual elements at one end of the bundle corresponding generally with that at the other end, each element otherwise extending between its ends substantially freely of other elements of the bundle. The elements are suitably held by individual threading through respective perforations of grill members (13) to pass into securement in associated tubes (14). Preferably the bundle has a sheath, wrapping, distinctively coloured element (11a) or other feature to indicate visually the relative rotational disposition of the bundle between its ends.

12 Claims, 1 Drawing Sheet

U.S. Patent
Oct. 18, 1994
5,356,434
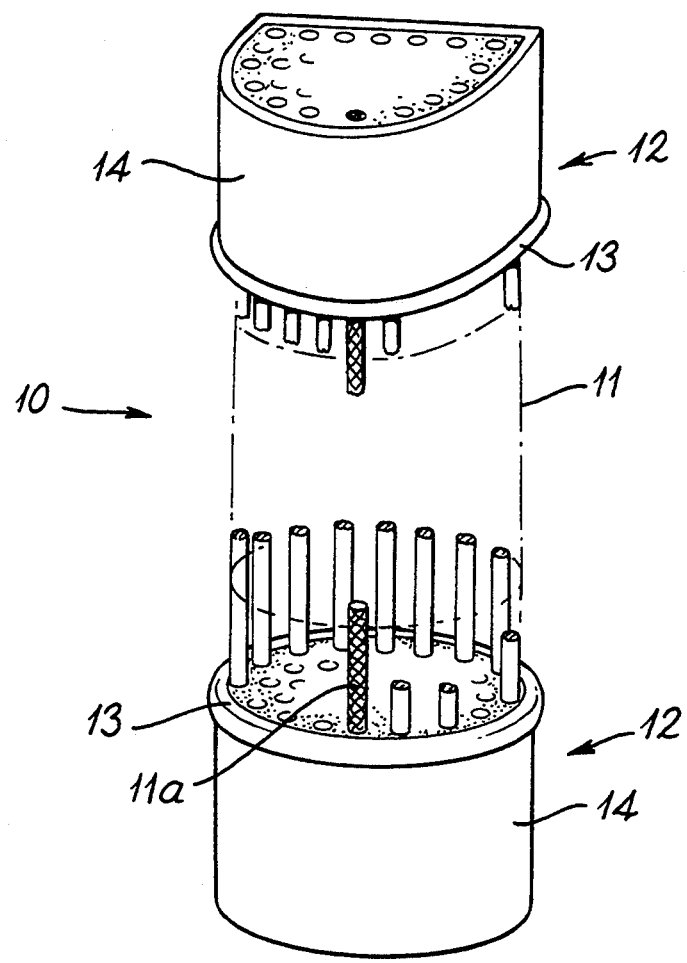

ARTIFICIAL LIGAMENTS

This invention concerns artificial ligaments and more particularly, but not exclusively, such ligaments for replacement of the cruciate ligaments of the knee.

Significant interest arose in the use of such ligaments about a decade ago, but the results have proved unreliable and many surgeons now prefer instead to use autologous grafts, mainly from muscle tendons, for ligament replacement.

The effective failure of artificial ligaments used to date may be explained by a new analysis which indicates that a satisfactory model for a cruciate ligament represented by a bundle of fibres co-extending between the femur and tibia should exhibit changes in shape and strain distribution in association with the relative rotation and translation which occur between those bones during flexion-extension movement or the knee. More particularly, this analysis shows that the changes in shape and strain distribution depend, during passive movement and under load, on the relationship between the respective distributions of ligament fibre attachments on the two bones interconnected by the ligament, i.e. on what can be termed the fibre mapping.

Further details of this analysis are given in a series of papers by O'Connor et al in Chapters 10, 11 and 12 of Knee Ligaments: Structure, Function, Injury and Repair p. 163–218 Raven Press, New York 1990, and also in Chapter 25, entitled "Kinematics and Mechanics of the Cruciate Ligaments of the Knee" by 0'Connor J. J. and Zavatsky A. in The Biomechanics of Diathrodial Joints, Vol. 2, Pages 197–252, edited by V. C. Mow, A. R. Cliffe and F. L-Y Woo, Springer Veragg, New York, 1990, the contents of which are hereby incorporated by reference. The analysis described therein was presented at the First World Congress on Biomechanics San Diego, Calif., 1990.

In any event prior artificial ligaments do not conform with this analysis. They have, tot example, commonly involved an overall woven or otherwise transversely interconnected structure and this can be seen to represent a contradiction to the generation of changes as indicated above in that there will necessarily be a counterproductive interaction between longitudinal elements of the structure which should otherwise tend to move or tense in an effectively independent and differential manner.

An object of the present invention is to improve this situation and to this end, in a general aspect, the invention provides an artificial ligament having a structure which can function n general conformity with the above analysis and so more closely simulate a natural ligament.

In a more particular aspect the invention provides an artificial ligament comprising a bundle of coextensive elongate elements that are held at their opposite ends in a mutual one-to-one relationship by respective attachment means suitable for securement in bone, with the relative disposition of the individual elements at one end of the bundle corresponding generally with that at the other end, each element otherwise extending between the points of connection to said attachment means substantially freely of other elements of the bundle.

Conveniently, each attachment means comprises a grill and a tube, the grill allowing the elements to be threaded individually through respective perforations thereof prior to being secured in the tube.

Also, it is preferable that such attachment means have cross-sectional forms which approximate the natural attachment areas of the relevant ligament. Thus, for the anterior cruciate ligament, the means are appropriately elliptic and semi-circular to approximate the attachment areas on he tibia and femur respectively.

It may also be appropriate to provide the main lengths of the elements in the bundle with a sheath, wrapping or some other additional feature, such as a distinctively coloured element, to indicate the relative rotational dispositions of the bundle ends when deployed during surgery. This will facilitate avoidance of deployment with an undesirable or additional twist relative to the natural situation which is to be simulated, and the sheath or other feature can, if appropriate, be disposable thereafter.

One embodiment of an artificial ligament as so far proposed according to the invention is diagrammatically illustrated, by way of example, in the accompanying drawing.

The illustrated ligament is for use as a replacement for the natural anterior cruciate ligament and is denoted generally at 10. The ligament 10 has a bundle of coextensive elongate elements 11 of which the opposite ends are held in respective similar attachment means 12. Each attachment means includes a grill member 13 through respective perforations of which individual elements of the bundle are threaded for securement in a tube 14 connected with the grill member. The grill members 13 have respectively different, elliptic and semi-circular, overall shape.

The elements of the bundle are seen to be of a monofilamentary form and so there is a one-to-one relationship between the elements at the ends of the bundle. More particularly, the relative disposition of the individual elements at one end of the bundle corresponds generally with that at the other end, without the intervening lengths of the elements being woven or otherwise subject to a transversely interacting relationship. In the result the ligament can assume a disposition in which the bundle is non-twisted and the two ends of each element of the bundle assume a generally corresponding position in the respective grill members, be it at the front, back, to one side, centre, and so on, notwithstanding the fact that the grill member may have somewhat different overall shapes.

In this last connection, the attainment of a non-twisted disposition or, for that matter, a disposition with a given order of twist can, in general, be visually confirmed by reference to a distinctively coloured element 11a in the bundle. The main lengths of the elements in the bundle can conveniently be provided with a sheath or wrapping 15.

The proposed ligament can be made of materials chosen from those used in prior ligaments which have proved unreliable for reasons of overall configuration or factors other than a deficiency in mechanical properties or biocompatibility. Use can also, of course, be made of materials developed for this or related purposes in due course. In either event, it is to be noted that, insofar as the elongate elements act relatively independent manner, they can differ individually in cross-sectional area, density, modulus of elasticity, and other ways with a view to providing an overall structure which more closely simulates the natural ligament to be replaced.

Similarly, prior or new techniques can be used for the purposes of securement of the attachment means in bone.

Also, ligament can be implanted in a uniform or varying tensile state through the bundle dependent on the disposition of the joint during surgery.

The invention is, of course, open to variation within the scope of the appended claims. For example, while the elements of the proposed ligament are suitably of a monofilamentary form, composite muitfilamentary forms of element are also possible to the extent that interaction between the constituent filaments during joint movement will be confined to the individual elements rather than extend transversely through the ligament. Also, use may be made of attachment means which are not intended for securement in bone, but are disposable after the bundle ends are so secured. Again, while particular reference has been made to the cruciate ligaments of the knee, the invention is applicable to the replacement of other ligaments for which a similiar analysis is relevant.

We claim:

1. An implantable artificial ligament for attachment to a human joint that generally exhibits changes in shape and strain distribution in association with relative rotation and translation between bones of the joint during flexion-extension movement of the joint, said artificial ligament comprising a bundle of coextensive elongate elements, each of said elements having a first end and a second end, each first end being held in mutual one-to-one relationship with the second end of that element, each of said first and second ends of each of said elements being attached to respective attachment means adapted to be secured to respective bones of the joint, the relative disposition of the individual elements at their respective first ends corresponding generally with the relative disposition of the individual elements at their respective second ends, each element extending between the respective attachment means substantially independently of other elements of the bundle.

2. A ligament according to claim 1 wherein each attachment means comprises a perforated member having a plurality of perforations and mounted to a tubular component, ends of said elements being individually threaded through respective perforations of the respective perforated member to pass into the tubular component and being secured therewithin.

3. A ligament according to claim 1 or 2 wherein each attachment means has a cross-sectional shape which substantially corresponds to that of a respective natural bone attachment area.

4. A ligament according to claim 3 for anterior cruciate usage wherein one of the respective attachment means is of generally elliptic cross-sectional form and the other is of generally semi-circular cross-sectional-form.

5. A ligament according to claim 1 further comprising means for providing a visual indication of the relative rotational disposition of the elements in the bundle.

6. A ligament according to claim 5 wherein the visual indication means comprises a differential coloring of one of the elements.

7. A ligament according to claim 5 wherein a sheath is disposed in surrounding relation to the bundle.

8. A ligament according to claim 7 wherein the sheath is disposable.

9. An artificial ligament comprising:
a plurality of substantially coextensive elongate elements, each said element having a first end and a second end;
a first attachment means secured to said first ends of said elements for securing and positioning said first ends in a first, non-planar array having an outer peripheral boundary, said first ends being substantially uniformly distributed throughout an area defined by said outer peripheral boundary;
a second attachment means secured to said second ends of said elements for securing and positioning said second ends in a second, non-planar array having an outer peripheral boundary, said second ends elements being substantially uniformly distributed throughout an area defined by said outer peripheral boundary; and
said elements being substantially free of mechanical interconnection to one another intermediate said first and second ends thereof.

10. A ligament according to claim 9, wherein each attachment means comprises a perforated member having a plurality of perforations and mounted to a tubular component, ends of said elements being individually threaded through respective perforations of the respective perforated member to pass into the tubular component and being secured therewithin.

11. A ligament according to claim 9 or 10 wherein each attachment means has a cross-sectional shape which substantially corresponds to that of a respective natural bone attachment area.

12. A ligament according to claim 11 for anterior cruciate usage wherein one of the respective attachment means is of generally elliptic cross-sectional form and the other is of generally semi-circular cross-sectional form.

* * * * *